United States Patent [19]

Chen et al.

[11] Patent Number: 5,561,095
[45] Date of Patent: Oct. 1, 1996

[54] SUPPORTED LEWIS ACID CATALYSTS FOR HYDROCARBON CONVERSION REACTIONS

[75] Inventors: Frank J. Chen; Christophe Le Deore, both of Edison, N.J.; Roger Spitz, Serezin; Alan Guyot, Lyon, both of France

[73] Assignee: Exxon Chemical Patents Inc., Linden, N.J.

[21] Appl. No.: 221,202

[22] Filed: Mar. 31, 1994

[51] Int. Cl.⁶ ........................................ B01J 31/00
[52] U.S. Cl. .................... 502/169; 502/150; 502/202; 502/203; 502/224
[58] Field of Search ............................. 502/150, 169, 502/202, 203, 224

[56] References Cited

U.S. PATENT DOCUMENTS

| | | | |
|---|---|---|---|
| 3,539,633 | 11/1970 | Piasek et al. | |
| 3,629,150 | 12/1971 | Addy et al. | 252/442 |
| 3,649,229 | 3/1972 | Otto. | |
| 4,025,403 | 5/1977 | Marek et al. | 204/159.24 |
| 4,426,317 | 1/1984 | Rogers | 502/150 |
| 4,476,343 | 10/1984 | Johnson | 585/530 |
| 4,487,846 | 12/1984 | Bailly et al. | 502/169 |
| 4,520,122 | 5/1985 | Arena | 502/150 |
| 4,613,580 | 9/1986 | Frame | 502/117 |
| 4,719,190 | 1/1988 | Drago et al. | 502/64 |
| 4,737,479 | 4/1988 | Frame et al. | 502/117 |
| 4,737,480 | 4/1988 | Frame et al. | 502/117 |
| 4,740,652 | 4/1988 | Frame | 585/512 |
| 4,795,851 | 1/1989 | Frame et al. | 585/512 |
| 4,795,852 | 1/1989 | Frame et al. | 585/512 |
| 4,798,667 | 1/1989 | Drago et al. | 208/117 |
| 4,835,331 | 5/1989 | Hammershaimb et al. | 585/520 |
| 4,929,800 | 5/1990 | Drago et al. | 585/744 |
| 4,935,565 | 6/1990 | Harley et al. | 570/258 |
| 5,019,652 | 5/1991 | Taylor et al. | 562/549 |
| 5,292,986 | 3/1994 | Abbott | 502/169 |
| 5,294,578 | 3/1994 | Ho et al. | 502/62 |
| 5,326,920 | 7/1994 | Ho et al. | 585/528 |

FOREIGN PATENT DOCUMENTS

| | | |
|---|---|---|
| 770656 | 10/1967 | Canada. |
| 0436775A2 | 7/1991 | European Pat. Off.. |
| 0609123 | 8/1994 | European Pat. Off.. |
| 2658498 | 8/1981 | France. |
| 225423 | 7/1985 | German Dem. Rep.. |
| 70-02055 | 8/1971 | Netherlands. |
| WO90/08118 | 7/1990 | WIPO. |

OTHER PUBLICATIONS

"Metal Halide and Organometal Halide Catalyzed Copolymerization and Cyclocodimerization of Acrylonitrile and Butadiene", W. Kuran, Stanislaw Pasynkiewicz, and Zbigniew Florjanczyk Die Makromolekulare Chemie 154 (1972) 71–79.

*Primary Examiner*—Asok Pal
*Assistant Examiner*—E. D. Irzinski
*Attorney, Agent, or Firm*—Harvey L. Cohen

[57] ABSTRACT

A supported Lewis acid catalyst system for catalyzing hydrocarbon conversion reactions including cationic polymerization, alkylation, isomerization and cracking reactions is disclosed, wherein the catalyst system comprises an inorganic oxide support having immobilized thereon at least one relatively strong Lewis acid and at least one relatively weak Lewis acid.

7 Claims, No Drawings

SUPPORTED LEWIS ACID CATALYSTS FOR HYDROCARBON CONVERSION REACTIONS

TECHNICAL FIELD

This invention relates to supported Lewis acid catalyst systems, to processes for preparing the catalyst systems, and to various hydrocarbon conversion reactions which are performed in the presence of such catalyst systems. More particularly, the invention relates to effective catalyst systems for cationic polymerization, alkylation, isomerization and hydrocarbon cracking reactions comprising at least two Lewis acids immobilized on an inorganic substrate containing surface hydroxyl groups, wherein at least one of the Lewis acids is a relatively strong Lewis acid and at least one of the Lewis acids is a relatively weak Lewis acid.

BACKGROUND OF THE INVENTION

Lewis acids are among the most powerful initiators for hydrocarbon conversion reactions. Such catalysts have been used in liquid, gaseous and solid form, and have been supported or immobilized on various polymeric and inorganic substrates, including, for example, silica gel, alumina, graphite and various clays.

Both supported and unsupported Lewis acid catalysts have been used with varying degrees of success for initiating alkylation reactions and the carbocationic polymerization of olefins, such as isobutene. However, in spite of the advances made in the fields of alkylation and polymerization catalysis, there continues to be interest in developing highly efficient catalyst systems which can be recycled or reused in hydrocarbon conversion processes. The present invention was developed pursuant to this interest.

SUMMARY OF THE INVENTION

In accordance with one aspect of the present invention, there is provided an immobilized Lewis acid catalyst system which is free from any added titanium-, vanadium-, hafnium- and zirconium-containing Lewis acids and which is active for various hydrocarbon conversion reactions, including, in particular, carbocationic olefin polymerizations and alkylation reactions. According to this aspect, the immobilized catalyst system is in the form of a particulate inorganic substrate on which there is supported or immobilized at least two separate Lewis acids, wherein at least one of the Lewis acids comprises a strong Lewis acid, such as an alkyl aluminum, an alkyl aluminum halide, an aluminum halide or a boron halide, and wherein at least one of the Lewis acids comprises a weak Lewis acid, such as a magnesium halide, an alkyl magnesium halide, an iron halide, a tin halide or aralkyl zinc. The particulate inorganic substrate which is to be used as the catalyst support may comprise any conventional inorganic substrate having surface hydroxyl groups, i.e., —OH groups. Such substrates include, for example, powders comprised of or including silica, alumina, magnesia, titania, zeolites, silica-alumina, silica-titania, silica-magnesia or the like.

In another aspect, an immobilized Lewis acid catalyst system may be prepared by reacting an inorganic, silicon-containing substrate having surface silanol groups, i.e., Si—OH groups, with both a relatively strong Lewis acid and a relatively weak Lewis acid, such that a first portion of the silanol groups on the substrate are converted to Si—O—M groups, where M is a metal ion derived from the relatively strong Lewis acid, and such that a second portion of the silanol groups are converted to Si—O—M', where M' is a metal ion derived from the relatively weak Lewis acid. In this aspect, it is not critical whether the inorganic substrate is first contacted with the strong Lewis acid or with the weak Lewis acid. Also in connection with this aspect, depending upon the identity of the strong and weak Lewis acids that are utilized, it may be desirable to contact the catalyst system with a halogenating agent, such as an alkyl chloride, hydrogen chloride, chlorine or the like, in order to control its acidity.

Another aspect of the present invention provides a process for using the above immobilized Lewis acid catalyst system, which is free from any added titanium-, vanadium-, hafnium- and zirconium-containing Lewis acids, for polymerizing a variety of monomers into homopolymers and copolymers, e.g., polyalkenes, by contacting the monomers with the immobilized Lewis acid catalyst system of this invention under carbocationic polymerization conditions. The monomers which may be used according to this aspect of the invention include those having unsaturation which are conventionally polymerizable using carbocationic Lewis acid catalyst polymerization techniques, such as, for example, olefins characterized by the presence in their structure of the group $>C=CH_2$. The catalyst system in this aspect is preferably free from any added titanium-, vanadium-, hafnium- and zirconium-containing Lewis acids which are known to catalyze Ziegler-type polymerization reactions and to produce primarily stereoregular polymers, as opposed to the generally amorphous polymers which are produced in accordance with the cationic polymerization process contemplated herein. To effect the present cationic polymerization process, in a preferred process, at least one inlet stream comprising monomer feed to be polymerized is fed to a reactor having at least one discharge stream. The monomer stream is polymerized in the reactor in the presence of the above-described immobilized Lewis acid catalyst system. The resulting polymerized polymer is removed from the reactor along with the unreacted monomers in the discharge stream while the immobilized catalyst system is retained in the reactor.

Yet another aspect of the invention is the preparation of a unique olefin polymer product which is characterized by having a high degree of reactive vinylidene unsaturation. In this aspect, it has been found, for example, that at least 40% of the polymer chains of polyisobutylene which has been prepared by cationic polymerization in the presence of the above-described Lewis acid catalyst systems exhibit terminal or non-terminal vinylidene unsaturation. In contradistinction, typically less than about 20% of the polymer chains of polyisobutylene prepared using a conventional non-supported strong Lewis acid catalyst, e.g., ethyl aluminum dichloride Lewis acid catalyst, will contain terminal or non-terminal vinylidene unsaturation.

In still other aspects, the catalyst systems of this invention may be used in hydrocarbon conversion processes such as isomerization, cracking and alkylation. As is known in the art, alkylation may be simply described as the addition or insertion of an alkyl group into a substrate molecule. Of particular interest is the alkylation of aromatic and hydroxy aromatic substrates, such as benzene, toluene, xylene and phenol. Suitable alkylating agents include, for example, olefins, alkanes, alkyl halides and mixtures. However, particularly preferred alkylating agents for use in the present invention include olefins, including olefin oligomers, such as propylene oligomers, having from about 6 to about 50 carbon atoms and having one double bond per molecule.

A significant advantage of the present catalyst systems is that they are stable and do not leach or otherwise deposit free Lewis acid into the reaction medium or, more importantly, into the reaction products. Another advantage is that the present catalyst systems are usable for multiple reaction cycles (in the context of a batch process) without regeneration, resulting in substantial cost savings, as well as the elimination of significant amounts of hazardous waste typically generated in conventional Lewis acid processes. Not only can the supported Lewis acid catalyst systems of the present invention be employed in multiple batch reaction cycles or on a continuous basis, but they can also be recovered readily during hydrocarbon conversion processes such as polymerization, alkylation, isomerization and alkylation by simple filtration techniques.

DETAILED DESCRIPTION OF THE PREFERRED EMBODIMENTS

The novel immobilized Lewis acid catalyst systems of the present invention may be prepared by fixing or immobilizing at least two Lewis acids on the surface of an inorganic substrate which contains surface —OH groups, wherein at least one of the Lewis acids is a relatively strong Lewis acid and at least one of the Lewis acids is a relatively weak Lewis acid. Generally, the metal of each Lewis acid will differ.

For the purposes of this invention the terms fixed or immobilized are used interchangeably and are defined as wherein substantially all of the active two Lewis acids are chemically bound to the substrate, e.g., by forming —O—metal bonds with the metals of the Lewis acids. In other words, the Lewis acids are not readily extracted by a solvent or diluent under conditions of polymerization, alkylation, isomerization or cracking.

The acid strength of a Lewis acid is dependent both upon the metal atom in the Lewis acid and upon the electronic effect of the ligand that is associated with the metal atom, and can be measured by reacting the Lewis acid with a base, typically a ketone or nitrile, and the observing by infra-red spectroscopy the shift of the characteristic absorption ν C=O or ν C≡N. The weaker Lewis acids give a low absorption shift, whereas the stronger Lewis acids give a higher shift. See, for example, W. Kuran et al., Makromol. Chem., 154, pp. 71–79 (1972), which discusses the relative strengths of Lewis acids in the context of metal halide and organometal halide catalyzed copolymerization and cyclodimerization of acrylonitrile and butadiene.

As a general rule, for the purposes of this specification and claims, the acid strength of a Lewis acid having a halogen ligand and a given metal central atom, such as $AlCl_3$ or $C_2H_5AlCl_2$, increases with the number of halogen atoms. Thus, the relative strength of aluminum and halogen-containing Lewis acids increases as follows:

Another general rule for the purposes of this invention is that the strength of a halide-containing Lewis acid of a given halide ligand, such as a chloride, increases in strength as follows:

$BCl_3$ stronger than (>) $AlCl_3$>$SnCl_4$>$MgCl_2$

Also, whatever the ligand, the magnesium-containing Lewis acids are weaker strength Lewis acids that are the aluminum-containing Lewis acids.

Thus, among the relatively strong Lewis acids which are contemplated for use in this invention, there may be included the halides, alkyl halides and alkyl compounds of aluminum, the halides of boron, and equivalents thereof. Preferred strong Lewis acids include, for example, aluminum compounds having the formula $R_nAlX_{3-n}$, where R is a monovalent hydrocarbon radical, preferably $C_1$–$C_{12}$ alkyl or aryl, n is a number from 0 to 3, and X is a halogen independently selected from the group consisting of fluorine, chlorine, bromine and iodine. Non-limiting examples of such preferred strong Lewis acids include triethyl aluminum (($C_2H_5$)$_3$Al), diethyl aluminum chloride (($C_2H_5$)$_2$AlCl), ethyl aluminum dichloride ($C_2H_5AlCl_2$), ethyl aluminum sesquichloride (($C_2H_5$)$_{1.5}$AlCl$_{1.5}$), aluminum chloride ($AlCl_3$) and mixtures thereof.

Among the relatively weak Lewis acids contemplated for use in this invention are the halides, alkyl halides and alkyl compounds of magnesium, iron, tin, zinc and equivalents thereof, including, for example, magnesium compounds having the formula $R^1_mMgX^1_{2-m}$, where $R^1$ is a monovalent hydrocarbon radical, preferably $C_1$–$C_{12}$ alkyl or aryl, m is 1 or 2, and $X^1$ is a halogen independently selected from the group consisting of fluorine, chlorine, bromine and iodine. Non-limiting examples of such preferred weak Lewis acids include dibutyl magnesium (($C_4H_9$)$_2$Mg), butyl magnesium chloride ($C_4H_9MgCl$), $SnCl_4$ and mixtures thereof.

The concentration of total Lewis acid (strong plus weak) present on the substrate will range from about 0.5 to about 20% by weight, based on total weight of the metal or metals of the Lewis acids; preferably from about 1 to about 10%; most preferably from about 2 to about 8%; for example, about 5 weight % of total Lewis acid metal on the substrate. The molar ratio of strong Lewis acid to weak Lewis acid is generally in the range of from about 100:1 to about 1:100; preferably from about 50:1 to about 1:50; most preferably from about 10:1 to about 1:10.

As indicated above, titanium-, vanadium-, hafnium-, and zirconium-containing Lewis acids, such as $TiCl_3$, $VCl_4$, and $HfCl_4$ and $ZrCl_4$ should be avoided inasmuch as they promote Ziegler-type catalysis.

The substrates to which the strong and weak Lewis acids may be fixed include any of the conventional inorganic oxide substrates which contain free hydroxyl groups which can react with the selected Lewis acids. Generally speaking any metal oxide which has surface hydroxyl groups can be utilized as the substrate. The terms "metal oxide" and "inorganic oxide", although typically used herein in the singular, are meant to include single oxides, such as silica or alumina, as well plural and complex oxides, such as silica-alumina, silica-alumina-thoria, zeolites and clays.

Non-limiting examples of such inorganic oxides include silica, alumina, titania, magnesia, silica-alumina, silica-titania, silica-magnesia, silica-alumina-thoria, silica-alumina-zirconia, crystalline aluminosilicates, including synthetic zeolites such as, for example, A, X, and ZSM-5 zeolites, and naturally occurring zeolites such as, for example, faujasite and mordenite, and open lattice clays, such as bentonire and montmorillonite. The preferred inorganic oxide substrates typically are in the form of powders or particles, and include a major component of silica or alumina or a mixture of both.

Particularly suitable as substrates are those solid inorganic oxide compositions known as metal oxide gels or gel oxides. Preferred oxide gel materials include those gel materials selected from the group consisting of silica, alumina, alumina-silica, zeolites and open lattice clays. Silica gel and silica-alumina gel substrates are particularly preferred.

The particular substrate materials are not critical, provided that they do not interfere with the conversion processes for which the resulting immobilized Lewis acid catalyst systems are intended to be used, and provided that they contain the hydroxyl groups which are necessary to react with, and thereby fix or immobilize, the Lewis acid catalyst materials.

The Lewis acids may be immobilized on the inorganic substrate by contacting the substrate with the selected Lewis acids at a temperature ranging from room temperature to elevated temperatures on the order of about 150° to 200° C. or higher, and preferably, from about room temperature to about 110° C. The substrate may be contacted first with the strong Lewis acid and then with the weak Lewis acid. Alternatively, the substrate may be contacted first with the weak Lewis acid, and then with the strong Lewis acid. Also, the substrate may be contacted simultaneously with both the strong and the weak Lewis acids. Also, depending upon the acidity of the substrate after having been contacted with the strong and weak Lewis acids, it may be desirable to further contact the substrate with a halogenating agent to convert residual hydrocarbyl radicals to halogen moieties. In this latter instance, the halogenating agents which may be employed include, for example, alkyl halides, halogens, hydrogen halides. Non-limiting examples of suitable halogenating agents include HCl, $Cl_2$ and compounds having the formula $R^2Cl$, where $R^2$ is a hydrocarbon radical, typically a $C_2$–$C_{10}$, preferably a $C_2$–$C_5$, secondary or tertiary alkyl radical, e.g., t-butyl chloride.

Immobilization of the strong and weak Lewis acids in accordance with preferred aspects of the present invention may be illustrated by the following schematic reaction sequencs:

(1)

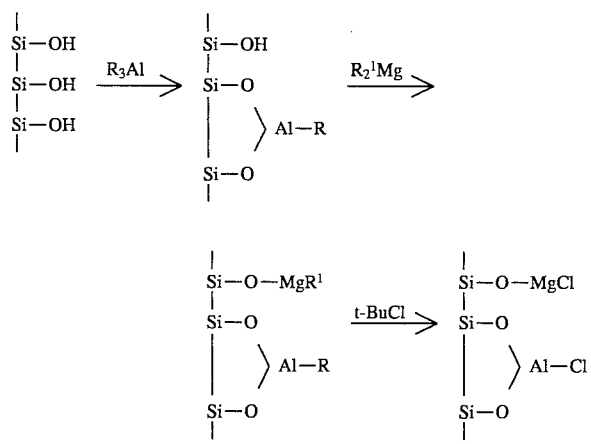

(2)

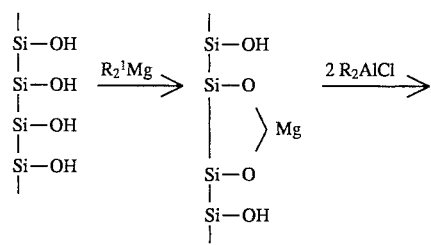

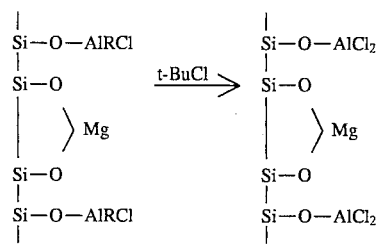

(3)

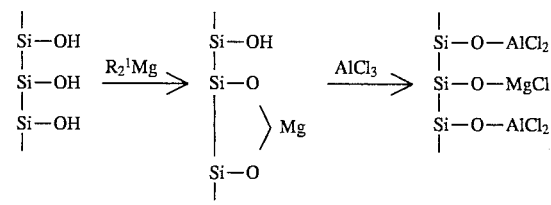

The novel immobilized catalysts of the present invention can be used to polymerize a variety of monomers into homopolymers and copolymers, e.g., polyalkenes. The monomers include those having unsaturation which are conventionally polymerizable using carbocationic Lewis acid catalyst polymerization techniques, and monomers which are the equivalents thereof. The terms cationic and carbocationic are used interchangeably herein. Olefin monomers useful in the practice of the present invention are polymerizable olefin monomers characterized by the presence of one or more ethylenically unsaturated groups. The monomers can be straight or branched monoolefinic monomers, such as vinyl ethers, propylene, 1-butene, isobutylene, and 1-octene, or cyclic or acyclic conjugated or non-conjugated dienes.

Suitable olefin monomers are preferably polymerizable terminal olefins; that is, olefins characterized by the presence in their structure of the group >C=$CH_2$. However, polymerizable internal olefin monomers (sometimes referred to in the patent literature as medial olefins) characterized by the presence within their structure of the group

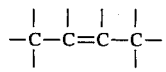

can also be used to form polymer products. When internal olefin monomers are employed, they normally will be employed with terminal olefins to produce polyalkenes which are interpolymers. For purposes of the invention, when a particular polymerized olefin monomer can be classified as both a terminal olefin and an internal olefin, it will be deemed to be a terminal olefin. Thus, 1,3-pentadiene (i.e., piperylene) is deemed to be a terminal olefin for purposes of this invention.

Preferred monomers used in the method for forming a polymer in accordance with the present invention are preferably selected from the group consisting of alpha-olefins and typically $C_3$–$C_{25}$ alpha olefins. Suitable alpha-olefins may be branched or straight chain, cyclic, and aromatic substituted or unsubstituted, and are preferably $C_3$–$C_{16}$ alpha-olefins. Mixed olefins can be used (e.g., mixed butenes).

The alpha-olefins, when substituted, may be directly aromatic substituted on the 2-carbon position (e.g., monomers such as $CH_2=CH-C_6H_5$ may be employed). Representative of such monomers include styrene, and derivatives such as alpha-methyl styrene, para-methyl styrene, vinyl toluene and its isomers.

In addition, substituted alpha-olefins include compounds of the formula $H_2C=CH-R^3-X^2$ wherein $R^3$ represents $C_1$ to $C_{22}$ alkyl, preferably $C_1$ to $C_{10}$ alkyl, and $X^2$ represents a substituent on $R^3$ and can be aryl, alkaryl, or cycloalkyl. Exemplary of such $X^2$ substituents are aryl of 6 to 10 carbon atoms (e.g., phenyl, naphthyl and the like), cycloalkyl of 3 to 12 carbon atoms (e.g., cyclopropyl, cyclobutyl, cyclohexyl, cyclooctyl, cyclodecyl, cyclododecyl, and the like) and alkaryl of 7 to 15 carbon atoms (e.g., tolyl, xylyl, ethylphenyl, diethylphenyl, ethylnaphthyl, and the like). Also useful are bicyclic, substituted or unsubstituted olefins, such as indene and derivatives, and bridged alpha-olefins of which $C_1$-$C_9$ alkyl substituted norbornenes are preferred (e.g., 5-methyl-2-norbornene, 5-ethyl-2-norbornene, 5-(2'-ethylhexyl)-2-norbornene, and the like).

Illustrative non-limiting examples of preferred alpha-olefins are propylene, 1-butene, isobutene, 1-pentene, 1-hexene, 1-octene, and 1-dodecene.

Dienes suitable for purposes of this invention include straight chain, hydrocarbon diolefins or cycloalkenyl-substituted alkenes having about 6 to about 15 carbon atoms, including, for example, 1,4-hexadiene, 5-methyl-1,4-hexadiene, 1,3-cyclopentadiene, tetrahydroindene, dicyclopentadiene, 5-methylene-2-norbornene, 5-cyclohexylidene-2-norbornene, 5-vinyl-2-norbornene, allyl cyclohexene and vinyl cyclododecene.

Of the non-conjugated dienes typically used, the preferred dienes are dicylcopentadiene, methyl cyclopentadiene dimer, 1,4-hexadiene, 5-methylene-2-norbornene, and 5-ethylidene-2-norbornene. Particularly preferred diolefins are 5-ethylidene-2-norbornene and 1,4-hexadiene.

The polymers and copolymers which can be manufactured by the process of the present invention are those which can be manufactured by a carbocationic polymerization process and include but are not limited to polyalkenes, such as polyisobutene, poly(1-butene), polystyrene, isobutene styrene copolymers, and the like. The term copolymer as used herein is defined to mean a polymer comprising at least two different monomer units.

In particular, the immobilized catalysts of the present invention are especially useful for manufacturing polyisobutene and poly(1-butene) from feedstreams containing butene monomers. It is especially preferred to use refinery feed streams containing $C_4$ monomers, commonly referred to as Raffinate I and Raffinate II.

The polymers and copolymers which are manufactured using the immobilized Lewis acid catalyst system of the present invention may be referred to as reactive polymers in the sense that they are characterized by having terminal or non-terminal vinylidene unsaturation in at least 40% of their polymer chains. Substantial non-terminal vinylidene unsaturation in conventional Lewis acid catalyzed polymers has not been observed. This differs from polymer products which have been prepared using conventional non-supported Lewis acid catalysts wherein a single Lewis acid, such as ethyl aluminum dichloride, is employed (typically less than 20% of the chains of polymers of this type contain vinylidene unsaturation), as well as from polymer products prepared using conventional $BF_3$ catalysis (typically 40% or more of the polymer chains contain terminal vinylidene).

For purposes of this comparison, polyisobutylene polymer chains having terminal vinylidene unsaturation may be illustrated as follows:

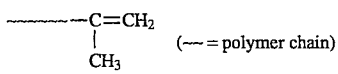

(—— = polymer chain)

Polyisobutylene polymer chains having non-terminal (internal) vinylidene unsaturation may be illustrated as follows:

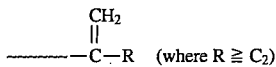

(where $R \geq C_2$)

The carbocationic polymerization process of the present invention may be carried out in a polar or, preferably, non-polar reaction medium as a continuous, semi-continuous or batch process. Suitable polar solvents which may be used as the polymerization reaction medium include, for example, methyl chloride, dichloromethane, ethyl chloride or nitromethane or the like, whereas suitable non-polar solvents include, for example, carbon tetrachloride, hexane, heptane, cyclohexane, and more generally the linear or branched, saturated or unsaturated hydrocarbon solvents which can be found in the stream of monomers obtained from various cracking processes.

The reactors which may be utilized in the practice of the present invention include conventional reactors and equivalents thereof such as batch reactors, stirred tank reactors, fluidized bed reactors, and continuous tank or tubular reactors and the like.

The reactor will contain sufficient amounts of the immobilized catalyst system of the present invention effective to catalyze the polymerization of the monomer containing feedstream such that a sufficient amount of polymer having desired characteristics is produced. The reaction conditions will be such that sufficient temperature, pressure and residence time are maintained effective to maintain the reaction medium in the liquid state and to produce the desired polymers having the desired characteristics.

Typically, the catalyst to monomer ratio utilized will be those conventional in this art for carbocationic polymerization processes. For example, catalyst to monomer mole ratios will typically be about 1/15000 to about 1/50, more typically about 1/5000 to about 1/100, and preferably about 1/1000 to about 1/200. This mole ratio will be calculated by determining the number of Lewis acid catalyst sites in the immobilized Lewis acid catalyst. This can be done by using conventional analytic testing techniques such as elemental analysis, NMR (e.g., aluminum NMR) and absorption spectroscopy. Once the number of Lewis acid sites per unit of immobilized catalyst is known, the mole ratio is calculated in a conventional manner.

The polymerization reaction temperature is conveniently selected based on the target polymer molecular weight and the monomer to be polymerized as well as standard process variable and economic considerations, e.g., rate, temperature control, etc. Typically temperatures from about $-100°$ C. to about $+75°$ C. are useful in the process; more typically about $-50°$ C. to about $+50°$ C, depending, as noted above, on polymer molecular weight. Reaction pressure will typically be about 200 kPA to about 1600 kPA, more typically about 300 to about 1200 kPA, and preferably about 400 to about 1000.

The monomer feedstream to this process may be at least one pure or mixed monomer feedstream or combinations thereof. Preferably, the monomer feedstream may be mixed with solvents such as hexane or heptane, and the like. A preferred feedstock to this process may be a pure or mixed refinery butene stream containing one or more of 1-butene, 2-butene, (cis and trans), and isobutene. The preferred feedstocks (preferred on an availability and economic basis) are available from refinery catalytic crackers and steam crackers. These processes are known in the art. The butene streams typically contain between about 6 wt. % to about 50 wt. % isobutylene together with 1-butene, cis- and trans-2-butene, isobutane and less than about 1 wt. % butadiene. One particularly preferred $C_4$ feedstream is derived from refinery catalytic or steam cracking processes and contains about 6–45 wt. % isobutylene, about 25–35 wt. % saturated butanes and about 15–50 wt. % 1- and 2-butenes. Another preferred $C_4$ feedstream is referred to as Raffinate II characterized by less than about 6 wt. % isobutylene.

The monomer feedstream is preferably substantially anhydrous, that is, it contains less than 50 ppm, and more preferably less than about 30 ppm, and most preferably less than about 10 ppm, by weight of water. Such low levels of water can be obtained by contacting the feedstream, prior to the reactor, with a water absorbent (such as NaH, $CaCl_2$, $CaSO_4$, molecular sieves and the like) or by the use of distillation drying.

The monomer feedstream is typically substantially free of any impurity which is adversely reactive with the catalyst under the polymerization conditions. For example, the monomer feed preferably should be substantially free of bases (such as caustic), sulfur-containing compounds (such as $H_2S$, COS, and organo-mercaptans, e.g., methyl mercaptan, ethyl mercaptan), N-containing compounds, and the like.

The monomer feedstream is typically substantially free of aromatic compounds to avoid alkylation reactions. Therefore, use of an aromatic solvent generally is not envisioned in this polymerization process.

A material acting as a cocatalyst (or promoter) may optionally be added to a monomer feedstock before that feed is introduced to a reactor or it may be added separately to the reactor, e.g., to the catalyst bed. A variety of conventional cocatalysts or equivalents can be used including inorganic acids such as hydrogen halides, lower alcohols, $C_2$–$C_{24}$ secondary or tertiary alkyl halides, organic acids such as carboxylic acids and sulfonic acids, and the like. For example, gaseous, anhydrous HCl, may be employed as a cocatalyst. The HCl will be employed in a catalytically effective amount, which amount will generally range from about 50 to 5,000 ppm by weight of the monomer feed, preferably 50 to 500 ppm (e.g., 70 to 200 ppm) by weight of the monomer feed when the monomer feed comprises >5 wt. % isobutylene, and preferably from about 100–5,000 ppm (e.g., 400–3,000 ppm) by weight when the feed comprises n-butenes and <5 wt. % isobutylene. If anhydrous HCl is added to the feedstream containing isobutene, t-butyl chloride is formed before contact with the solid catalyst.

The order of contacting the monomer feedstream, catalyst, cocatalyst (if any), and solvent is not critical to this invention. Accordingly, the catalyst and cocatalyst can be added to the reactor before or after adding the monomer feedstream and solvent. Alternatively, the catalyst and monomer feedstream can be added before or after adding the cocatalyst and solvent.

The degree of polymerization of polymers (and oligomers) produced with the catalyst of this invention will be determined by the desired end use. Typically the degree of polymerization is from about 5 to 5,000; more typically from about 10 to about 1,000; for low molecular weight polymers and oligomers the degree of polymerization will typically be about 5 to about 100. Correspondingly, the number average molecular weight, $M_n$, of a polymeric product will be determined by the monomer and degree of polymerization; for a $C_4$-based polymer, typical values are from about 300 to about 300,000 gm/mole, depending on the intended end use of the product. The range of number average molecular weight of lower molecular weight polymeric products will be from about 300 to about 16,000; more typically about 600 to about 6000 gm/mole. Number average molecular weight is conveniently measured by a suitably calibrated gel permeation chromatography (GPC) instrument. The polydispersity (PDI), also known as the molecular weight distribution $(M_w/M_n)$ will typically range from about 4 to about 25, more typically about 5 to about 22, and preferably about 6 to about 20. Unexpectedly, in some instances, a characteristic of the present catalyst system is that, during the couse of the polymerization, it produces two polymers, one being a low molecular weight polymer (Mn on the order of about 500) with a very narrow molecular weight distribution, and the other being a higher molecular weight (Mn typically on the order of about 2500 to about 6000) with a much broader molecular weight distribution.

Lewis acid catalysts of the present invention also find use in other hydrocarbon conversion processes including alkylation, isomerization and cracking. For example, the catalysts may be employed in the cracking of long chain hydrocarbons, e.g., heptane, butane, etc., to produce shorter chain products such as ethane, propane, butanes, etc. Additionally, the catalysts may be used to catalyze the isomerization of normal alkanes to their branched chain isomers.

The alkylation process of the present invention will be conducted by contacting the aromatic or hydroxy aromatic substrate and alkylating agent under reaction conditions, including mole ratio, temperature, time and catalyst ratio sufficient to alkylate the substrate.

The hydroxy aromatic substrate compounds useful in the preparation of the alkylated materials of this invention include those compounds having the formula:

wherein Ar represents

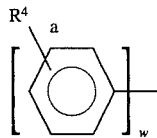

and z is an integer from 1 to 2, w is an integer from 1–3, a is 1 or 2 and $R^4$ is a $C_1$–$C_{24}$ alkyl radical.

Illustrative of such Ar groups are phenylene, biphenylene, naphthalene and the like.

The aromatic substrate compounds useful in the preparation of the alkylated materials of this invention include those compounds having the formulas:

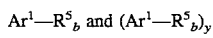

wherein $Ar^1$ represents:

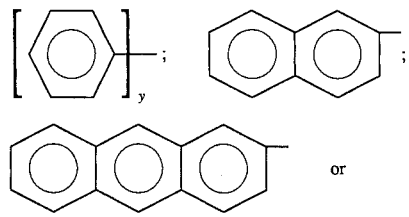

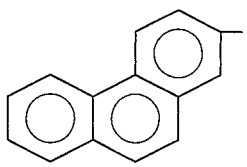

wherein b is one or two; $R^5$ is $C_1-C_{24}$ alkyl, $C_3-C_{24}$ cycloalkyl, $C_6-C_{18}$ aryl, $C_7-C_{30}$ alkylaryl, OH, or H; and y is 1–3.

Illustrative of such $Ar^1$ groups are benzene, phenylene, biphenylene, naphthalene, and anthracene.

The substrate generally will be contacted in a molar ratio of from about 0.1 to 10 preferably from about 1 to 7, more preferably from about 2 to 5, moles of the substrate per mole of the alkylating agent. Conventional ratios of alkylating agent typically will be used. The ratio typically will be about 0.5 to 2:1, more typically about 0.8 to about 1.5:1 and preferably about 0.9 to about 1.2:1. The selected catalyst can be employed in widely varying concentrations. Generally, the catalyst will be charged to provide at least about 0.001, preferably from about 0.01 to 0.5, more preferably from about 0.1 to 0.3, moles of Lewis acid catalyst per mole of substrate charged to the alkylation reaction zone. Use of greater than 1 mole of the Lewis acid catalyst per mole of substrate is not generally required. The reactants can be contacted with the present immobilized Lewis acid catalyst system employing any conventional solid-liquid contacting techniques, such as by passing the reactants through a fixed bed of catalyst particles. The upper limit on the moles of catalyst employed per mole of substrate compound is not critical.

The temperature for alkylation can also vary widely, and will typically range from about 10 to 250° C., preferably from about 20 to 150° C., more preferably from about 25 to 80° C.

The alkylation reaction time can vary and will generally be from about 1 to 5 hours, although longer or shorter times can also be employed. The alkylation process can be practiced in a batchwise, continuous or semicontinuous manner.

Alkylation processes of the above types are known and are described, for example, in U.S. Pat. Nos. 3,539,633 and 3,649,229, the disclosures of which are hereby incorporated by reference.

The invention will be understood more fully in conjunction with the following examples which are merely illustrative of the principles and practice thereof. The invention is not intended to be limited by these illustrative examples. Parts and percentages where used are parts and percentages by weight, unless specifically noted otherwise.

EXAMPLE 1

Catalyst Synthesis ($SiO_2$/TIBA/$MgBu_2$/t-BuCl Catalyst)

Silica (W. R. Grace 1952) having a specific area of 300 $m^2$/g was dehydrated by heating under vacuum at 450° C. for one hour. To 2.6 g of the dehydrated silica, there was added 0.9 mmol of triisobutyl aluminum (TIBA) in heptane. After one hour, 3 mmol of $MgBu_2$ (dibutyl magnesium) was added and the mixture was heated 20 minutes at 80° C. After washing the resulting solids three times with heptane, 2 ml of pure tertiary-butyl chloride (t-BuCl) was added and the silica was again washed several times with heptane. The silica-supported catalyst system, which was yellow in color, turned orange after drying under vacuum for $1.5$ hours at 100° C. The resulting dried catalyst system was analyzed and found to contain 1.47% Mg, 0.73% Al and 6.35% Cl.

EXAMPLE 2

Isobutene Polymerization (Runs 1–3)

In a glass flask equipped with a dropping funnel, a thermometer and a pressure transducer, there were placed 100 ml of heptane and the amount of isobutene monomer indicated in Table 1. To this mixture, maintained at −20° C., there was added an amount of the catalyst system prepared in Example 1 containing the indicated amount of aluminum. The contents of the flask were maintained at −20° C. for 40 minutes, after which the polymerization reaction was discontinued and the reaction products were analyzed by gel phase chromatography (GPC)in tetrahydrofuran (THF) using polystyrene as the standard. The results are set forth in Table 1 hereinbelow. The above procedure was repeated (Runs 2 and 3), except that the polymerization medium was first dried using NaH as a dessicant (Runs 2 and 3), the amounts of monomer (Runs 2 and 3) and catalyst (Run 3) were varied, as was the polymerization time (Run 2). Also, the temperature was permitted to vary over the course of the polymerization (Run 2). In the runs wherein NaH was used as a dessicant, about 0.1 to 0.5 g of NaH were introduced under an argon atmosphere from a Schlenck tube into the polymerization flask containing about 70 g of the heptane solvent medium. The monomer was then added to the flask and the mixture was allowed to stand for about 15 minutes before starting the polymerization. The results of Runs 2 and 3 are also set forth in Table 1.

TABLE 1

| Run No. | Monomer moles/l | aluminum mmoles/l | T, °C. | ΔT | Conv., % | Time min. | $M_n$ | $M_w$ |
|---|---|---|---|---|---|---|---|---|
| 1* | 2.5 | 0.35 | −20 | 0 | 56 | 40 | 2900 | 57160 |
| 2 | 2.8 | 0.35 | −20 | 21 | 44 | 10 | 2850 | 29100 |
| 3 | 3.2 | 0.2 | −20 | 0 | 51.5 | 40 | 2580 | 34500 |

*without NaH desiccant

It will be seen from the data in Table 1, that Run 2 (using NaH desiccant) resulted in a faster rate of conversion.

EXAMPLE 3

Catalyst Synthesis ($SiO_2$/$MgBu_2$/DEAC/t-BuCl Catalyst)

To 1.4 g of dehydrated silica (W. R.Grace 1952) in 50 ml of heptane, there was added 2.2 mmol of $MgBu_2$. After 2 hours at room temperature, the silica was washed and 3.7 mmol of diethyl aluminum chloride (DEAC) in heptane were added. After 2 hours, the silica was washed with heptane and 3 mmol of t-BuCl in heptane were added. After about 1 hour, the silica was washed and dried under a vacuum for 1.5 hours at 100° C.

EXAMPLE 4

Isobutene Polymerization (Runs 4–5).

The procedure of Example 2 was repeated, except the supported Lewis acid catalyst system prepared in Example 3 was employed in place of the catalyst system of Example 1. The polymerization procedure was run twice, once after using NaH as a desiccant to dry the solvent medium (Run 4) and once without dessicating the solvent medium (Run 5). The results of Runs 4 and 5 are set forth below in Table 2.

TABLE 2

| Run No. | Monomer moles/l | catalyst g/l | T, °C. | Conv., % | Time min. | $M_n$ | $M_w$ |
|---|---|---|---|---|---|---|---|
| 4* | 2.3 | 0.45 | −20 | 47.6 | 60 | 5580 | 72960 |
| 5 | 2.6 | 0.3 | −20 | 37.9 | 20 | 7550 | 101200 |

*without NaH desiccant

The data in Table 2 confirms the increased rate of conversion experienced when the polymerization is conducted in the presence of the NaH desiccant. The effect on the rate of conversion is relatively high, whereas the effect on the molecular weight is not as high.

EXAMPLE 5

Catalyst Synthesis ($SiO_2$/$MgBu_2$/$AlCl_3$ Catalyst

To 2.1 g of dehydrated silica (W. R. Grace 1952) in 60 ml of heptane there was added 2 ml of a 1 molar solution $MgBu_2$ in hexane. After one hour, a solution of 0.7 g of $AlCl_3$ in toluene were added. After heating for two hours at 80° C., the silica was washed several times with toluene. After drying under vacuum at 100° C. for one hour, the catalyst system was recovered as a green yellow powder. The catalyst was analyzed for 13.7% Cl, 3.9% Al and 1.2% Mg.

EXAMPLE 6

Isobutene Polymerization (Runs 6–9)

The procedure of Example 2 was repeated, except that the supported Lewis acid catalyst system prepared in accordance with Example 5 was used in place of the catalyst system of Example 1. The results of this example are set forth in Table 3.

EXAMPLE 7

Hexene-1 Oligomerization

To a glass flask, there was added 90 g of the catalyst system prepared in accordance with the procedure of Example 5 (in 50 ml of heptane). Thereafter, 1.4 ml of t-BuCl and 10 ml of hexene were added with stirring.

The mixture was stirred for 70 min at room temperature and the reaction was then stopped by filtration of the resulting suspension. The resulting solution was uncolored and no trace of silica could be seen. After evaporation of the solvent, 2.9 g of product was recovered, corresponding to about a 45% conversion to hexene-1 oligomer.

EXAMPLE 8

Toluene Alkylation

To a glass flask, there was added 272 mg of the catalyst system prepared in accordance with Example 5 (in 100 ml of toluene). There was then added 2 ml of tetrapropylene having one unsaturated bond per molecule. After stirring for ¼ hour at room temperature, the reaction was stopped by filtration of the resulting suspension. The conversion of tetrapropylene was calculated to be 95% by gas chromatography.

What is claimed is:

1. A supported Lewis acid catalyst that is free from added titanium-, vanadium-, hafnium- and zirconium-containing Lewis acids and is effective for catalyzing hydrocarbon conversion reactions, which comprises an inorganic oxide substrate having immobilized thereon a catalytically effective amount of at least one strong Lewis acid selected from the group consisting of the halides, alkyl halides and alkyl compound of aluminum and the halides of boron and at least one weak Lewis acid selected from the group consisting of the halides, alkyl halides and alkyl compounds of magnesium, iron, tin and zinc and wherein the molar ratio of strong Lewis acid to weak Lewis acid is in the range of from about 100:1 to about 1:100.

2. The catalyst according to claim 1, wherein said oxide substrate initially contains surface hydroxyl groups capable

TABLE 3

| Run No. | Monomer moles/l | catalyst g/l | T, °C. | Conv., % | Time min. | $M_n$ | $M_w$ |
|---|---|---|---|---|---|---|---|
| 6* | 2.17 | 0.45 | −20 | 36.4 | 30 | 9800 | 79870 |
| 7[1] | 2.54 | 0.36 | −20 | 37.4 | 30 | 12280 | 117140 |
| 8[2] | 2.8 | 0.38 | −20 | 61.3 | 30 | 15390 | 105560 |
| 9* | 2.7 | 0.5 | −40 | 25 | 60 | 6300 | 38000 |

*without NaH desiccant
[1]heptane-isobutene mixture maintained over NaH for 0.5 hours
[2]heptane-isobutene mixture maintained over NaH for 2 hours of reacting with and thereby immobilizing both said strong Lewis acid and said weak Lewis acid, wherein said strong Lewis acid is supported on said substrate by having been reacted with at least a first portion of said hydroxyl groups initially present on said substrate, and wherein said weak Lewis acid is supported on said substrate by having been reacted with at least a second portion of said hydroxyl groups initially present on said substrate and wherein the concentration of strong plus weak Lewis acid present on said substrate, based on the total weight of the metals of said Lewis acids, is from about 0.5 to about 20% by weight.

3. The catalyst system according to claim 2 wherein said inorganic oxide substrate comprises at least one silicon-containing oxide comprising surface Si—OH groups, a first portion of Si—O—M groups, where M represents an atom derived from a strong Lewis acid, and at least a second portion of Si—O—M' groups, where M' represents an atom derived from a weak Lewis acid.

4. The catalyst system according to claim 3, wherein M is selected from the group consisting of Al an boron, and wherein M' is selected from the group consisting of Mg, Fe, Sn and Zn.

5. The catalyst system according to any one of claim 4 wherein said inorganic oxide substrate comprises a silica component.

6. The catalyst system according to claim 5, wherein said silica component is selected from the group consisting of silica, silica-alumina, silica-titania, silica-magnesia, silica-alumina-thoria, silica-alumina-zirconia, crystalline aluminosilicates, open lattice clays and mixtures thereof.

7. A process for preparing a supported Lewis acid cationic polymerization and alkylation catalyst system, which comprises the steps of:

(a) providing an inorganic, hydroxyl group-containing support;

(b) contacting said support with a strong Lewis acid, other than titanium-, vanadium-, hafnium- and zirconium-containing Lewis acids, and selected from the group consisting of the halides, alkyl halides and alkyl compounds of aluminum and the halides of boron, under conditions effective to react said strong Lewis acid with a first portion of the hydroxyl groups contained on said support;

(c) either before or after step (b), contacting said support with a weak Lewis acid, other than titanium-, vanadium-, hafnium- and zirconium-containing Lewis acids, and selected from the group consisting of the halides, alkyl halides and alkyl compounds of magnesium, iron, tin, and zinc under conditions effective to react said weak Lewis acid with a second portion of the hydroxyl groups contained on said support; and (d) after steps (b) and (c), optionally contacting said support with a halogenating agent; and wherein the molar ratio of strong Lewis acid to weak Lewis acid is in the range of from about 100:1 to about 1:100.

* * * * *

UNITED STATES PATENT AND TRADEMARK OFFICE
CERTIFICATE OF CORRECTION

PATENT NO. : 5,561,095
DATED : October 1, 1996
INVENTOR(S) : Chen, et. al.

It is certified that error appears in the above-indentified patent and that said Letters Patent is hereby corrected as shown below:

Column 15, line 23 at claim 5, delete "any one of claim 4"

and insert --any one of claims 1 to 4,--.

Signed and Sealed this

Seventeenth Day of December, 1996

Attest:

BRUCE LEHMAN

*Attesting Officer*     *Commissioner of Patents and Trademarks*